United States Patent
Patel

(10) Patent No.: US 10,085,971 B2
(45) Date of Patent: Oct. 2, 2018

(54) PHARMACEUTICAL SOLUTION OF ASENAPINE FOR SUBLINGUAL OR BUCCAL USE

(71) Applicant: Mahendra R. Patel, Delray Beach, FL (US)

(72) Inventor: Mahendra R. Patel, Delray Beach, FL (US)

(73) Assignee: Navinta III Inc, Boca Raton, FL (US)

( * ) Notice: Subject to any disclaimer, the term of this patent is extended or adjusted under 35 U.S.C. 154(b) by 0 days.

(21) Appl. No.: 15/682,159

(22) Filed: Aug. 21, 2017

(65) Prior Publication Data

US 2018/0050017 A1 Feb. 22, 2018

Related U.S. Application Data

(60) Provisional application No. 62/378,018, filed on Aug. 22, 2016.

(51) Int. Cl.
| | |
|---|---|
| *A61K 31/407* | (2006.01) |
| *A61K 9/107* | (2006.01) |
| *A61K 47/10* | (2017.01) |
| *A61K 9/00* | (2006.01) |

(52) U.S. Cl.
CPC ............ *A61K 31/407* (2013.01); *A61K 9/006* (2013.01); *A61K 9/107* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 5,763,476 | A | 6/1998 | Delbressine et al. |
| 7,741,358 | B2 | 6/2010 | Heeres |
| 8,022,228 | B2 | 9/2011 | Heeres |
| 2008/0306133 | A1 | 12/2008 | van der Sterren et al. |
| 2014/0142158 | A1 | 5/2014 | Bertran et al. |
| 2017/0007537 | A1 | 1/2017 | Reddy et al. |

FOREIGN PATENT DOCUMENTS

| | | |
|---|---|---|
| CN | 104447771 A | 3/2015 |
| GB | 2461681 A | 1/2010 |
| GB | 2481407 A | 12/2011 |
| WO | 2009098318 A1 | 8/2009 |
| WO | 2010127674 A1 | 11/2010 |
| WO | 2014207664 A2 | 12/2014 |
| WO | 2015125152 A2 | 8/2015 |

OTHER PUBLICATIONS

Saphris® (asenapine) Prescription Information—© 2009, Schering Corporation. All rights reserved. pp. 1-38.
Saphris® (asenapine) Prescription Information Revisions—© 2013 Merck Sharp & Dohme B. V.; used by Actavis, Inc. or its affiliates under license. © 2015 Actavis. All rights reserved. The trademark SAPHRIS is used by Actavis, Inc. or its affiliates under license from Merck Sharp & Dohme B.V. All rights reserved. Revised Mar. 2015, pp. 1-38.

*Primary Examiner* — Savitha M Rao
*Assistant Examiner* — Gregg Polansky
(74) *Attorney, Agent, or Firm* — St. Onge Steward Johnston & Reens, LLC

(57) ABSTRACT

A kit for treating psychosis by administering a pharmaceutically acceptable liquid composition of Asenapine to oral mucosa includes a formulation having Asenapine, or a pharmaceutically acceptable salt or hydrate thereof, ethanol, and water and a multidose pump filled with the formulation. The Asenapine compositions are stable for an extended period of time at normal storage conditions.

19 Claims, No Drawings

PHARMACEUTICAL SOLUTION OF ASENAPINE FOR SUBLINGUAL OR BUCCAL USE

FIELD OF THE INVENTION

The present invention relates to pharmaceutical solutions of Asenapine and, particularly, Asenapine solutions for sublingual or buccal use. The invention also relates to methods of treating schizophrenia and psychosis by administering a therapeutically effective amount of the inventive Asenapine solutions.

BACKGROUND OF THE INVENTION

Asenapine belongs to the dibenzo-oxepino-pyrrole class of psychotropic agents and is a potent antagonist of dopamine and serotonin receptors. The maleate salt of Asenapine has been approved as a drug for the treatment of schizophrenia and psychosis in humans. During the clinical studies of Asenapine, it was observed that oral dosing of the drug in human patients was associated with serious cardiotoxic side effects including postural hypotension. However, further development demonstrated that these side effects can be minimized with sublingual or buccal delivery. This dosing regimen was extensively studied and a sublingual tablet form of Asenapine maleate is now available as Saphris® for human use.

As can be appreciated by those skilled in the art, the sublingual tablet formulation requires very specific physical properties of the drug substance and drug product since the drug must dissolve quickly in the small volume of saliva present in the mouth. It is reported that a sublingual tablet must disintegrate in less 30 seconds for good efficacy.

Two crystalline forms of Asenapine maleate are known. One form, commonly referred as form H, has monoclinic crystals and melts at 141-145° C. The crystals of other form, commonly called form L, are orthorhombic and melting point of 138-142° C. Form H crystals are easily produced by crystallization from ethanol and the particles of crystals are about 100 micron when viewed under a micrograph. These crystals do not have the desired dissolution profile for sublingual use. The L form crystals of are smaller and have the requisite physiochemical properties but must be produced under very specific crystallization procedure. In the past, micronization of form H to reduce the crystal size was also tried but during micronization form H (orthorhombic) is converted to form L (monoclinic) to varying degree. It has been very difficult to control this transformation. Since the two forms have such divergent physicochemical properties, a mixture with variable amounts of two forms cannot be used in the preparation of a uniform dosage form required for a commercial product. The currently marketed sublingual tablet of Saphris is made using form L in a complex lyophilization process.

Thus, there is a need for a simple sublingual dosage form of Asenapine amenable for commercial production.

US 2017/0007537, assigned to Hetero Research Foundation, discloses liquid spray compositions comprising Asenapine for administration through oral mucosa. These compositions rely on penetration enhancer, particularly diethylene glycol monoethyl ether. There is no indication if the formulations are stable for an extended period of time. A solution of Asenapine maleate in polyol such as propylene glycol develops a yellow color during storage and therefore is not suitable as a commercial dosage form.

WO 2010127674 discloses liquid pharmaceutical Asenapine formulations that can be aerosolized or sprayed. However, these formulations are for transdermal delivery.

There is still a need for liquid Asenapine formulations that can be delivered orally and that are simple to manufacture.

There is particularly a need for liquid Asenapine formulations that can be delivered orally and that have excellent stability.

There is further a need for liquid compositions of Asenapine that can be delivered orally in a multi dose device.

There is a need for oral liquid compositions of Asenapine that can be supplied for a month of dosing (60 doses).

SUMMARY OF THE INVENTION

The foregoing objectives are achieved by provision of pharmaceutically acceptable liquid compositions of Asenapine for sublingual or buccal delivery comprising Asenapine, or a pharmaceutically acceptable salt or hydrate thereof, ethanol, and water, wherein the compositions are stable for an extended period of time at normal storage conditions.

In some embodiments, the compositions comprise greater than about 10% by volume of ethanol. In certain of those embodiments, the composition comprises about 10% to about 80% by volume of ethanol. In some of those compositions, the composition comprises about 50% to about 70% by volume of ethanol.

In certain preferred embodiments, the Asenapine, or a pharmaceutically acceptable salt or hydrate thereof, is Asenapine maleate.

In some embodiments, the liquid compositions further comprise pharmaceutically acceptable excipients selected from one or more of preservatives, antioxidants, buffers, taste modifiers, flavors or combinations thereof.

In preferred embodiments, the composition comprises at least one of a preservative and antioxidant.

In certain preferred embodiments, the composition comprises EDTA and/or L-Methionine.

In preferred embodiments, the composition does not include a polyol. In some of those embodiments, the composition is free of propylene glycol.

In some embodiments, the composition exhibits no weight loss after storage at 25° C./60% RH for 7 days. In some embodiments, the composition exhibits less than 0.1% weight loss after storage at 25° C./60% RH for 7, 21, 28 and 35 days. In certain embodiments, the composition exhibits less than 0.3% weight loss after storage at 25° C./60% RH for 7, 14, 21, 28 and 35 days. In certain of those embodiments, the composition exhibits less than 0.07% weight loss after storage at 25° C./60% RH for up to 35 days.

In some embodiments, no solvent derived impurities are produced when the liquid Asenapine formulations are stored under ambient conditions for an extended period of time. In some of those embodiments, no solvent derived impurities are produced after 3 months storage of the formulation at 25° C. In some of those embodiments, no solvent derived impurities are produced after 6 months storage of the formulation at 25° C. In some preferred embodiments, no solvent derived impurities are produced after one year storage of the formulation at ambient (around 25° C./60% RH) conditions.

In certain of embodiments, the formulation produces less than 0.2% Asenapine N-oxide after 3 months storage of the formulation at 25° C. In some of those embodiments, the formulation produces less than 0.1% Asenapine N-oxide. In certain of those embodiments, the formulation produces less than 0.05% Asenapine N-oxide after 3 months storage of the formulation at 25° C. In certain of embodiments, the formulation produces less than 0.3% Asenapine N-oxide after 6 months storage of the formulation at 25° C. In some of those embodiments, the formulation produces less than 0.1% Asenapine N-oxide. In certain of those embodiments, the formulation produces less than 0.05% Asenapine N-oxide after 6 months storage of the formulation at 25° C.

In certain of embodiments, the formulation produces less than 0.2% deschloro Asenapine after 3 months storage of the formulation at 25° C. In some of those embodiments, the formulation produces less than 0.1% deschloro Asenapine. In certain of those embodiments, the formulation produces less than 0.05% deschloro Asenapine after 3 months storage of the formulation at 25° C. In certain of embodiments, the formulation produces less than 0.2% deschloro Asenapine after 6 months storage of the formulation at 25° C. In some of those embodiments, the formulation produces less than 0.1% deschloro Asenapine. In certain of those embodiments, the formulation produces less than 0.05% deschloro Asenapine after 6 months storage of the formulation at 25° C.

In some embodiments, the total concentration of all impurities in the final product is less than about 2.0% when the formulation is stored at ambient storage conditions for an extended period of time. In some of those embodiments, the formulation produces less than 0.5% total impurities after 3 months storage of the formulation at 25° C. In certain of those embodiments, the formulation produces less than 0.2% total impurities. In certain preferred embodiments, the formulation produces less than 0.1% total impurities after 3 months storage of the formulation at 25° C. In some of those embodiments, the formulation produces less than 1.0% total impurities after 6 months storage of the formulation at 25° C. In certain of those embodiments, the formulation produces less than 0.5% total impurities.

In another aspect, the invention provides a pharmaceutically acceptable liquid composition of Asenapine for sublingual or buccal delivery comprising Asenapine, or a pharmaceutically acceptable salt or hydrate thereof, greater than about 10% ethanol, and water.

In yet another aspect, the invention provides a method of treating psychosis by administering a therapeutically effective amount of the foregoing liquid Asenapine compositions to a patient in need thereof.

In some embodiments of the method, about 2.5 mg to about 10 mg Asenapine is delivered to a patient's mouth.

In certain embodiments of the method, about 140 μL of the composition is administered to a patient by spraying the liquid Asenapine compositions into the patient's mouth.

In yet a further aspect, the invention provides a kit for treating psychosis by administering a pharmaceutically acceptable liquid composition of Asenapine for sublingual or buccal delivery comprising: a formulation including Asenapine, a salt or hydrate thereof, ethanol, and water; and a multidose pump filled with the formulation.

In some embodiments, the pump delivers about 2.5 mg to about 10 mg of Asenapine per dose.

In certain embodiments, the pump contains 60 to 65 deliverable doses.

In an even further aspect, the invention provides a method of manufacturing a liquid Asenapine composition suitable for sublingual or buccal delivery comprising the steps of: dissolving Asenapine, or a pharmaceutically acceptable salt or hydrate thereof, in an ethanolic solution, optionally, adding a solution of EDTA and/or a solution of L-Methionine to the ethanolic Asenapine solution, stirring the mixture under $N_2$, filtering the resulting mixture, and filing the filtrate into a storage container.

DETAILED DESCRIPTION OF THE INVENTION

The present invention relates to liquid solutions of Asenapine for sublingual or buccal delivery. The solutions may be delivered via a metered dispensing system. The formulations are stable for an extended period of time at normal storage conditions.

The term "Asenapine" as used herein refers to trans-5-chloro-2-methyl-2,3,3a, 12b-tetrahydro-1 H-dibenz[2,3:6,7] oxepino-[4,5-c]pyrrole. It has two optically active centers leading to two isomers: (3afi, 12bR)-5-Chloro-2,3,3a, 12b-tetrahydro-2-methyl-1H-dibenz[2,3:6,7]oxepino[4,5-c]pyrrole. Asenapine may be use in any form including any of its enantiomers or mesoforms, any mixture thereof including Asenapine in racemic form, any Asenapine salt, Asenapine (or any of its enantiomers, or mixtures thereof of Asenapine or salts of Asenapine) in any crystal form, amorphous or polymorphous form, in any solvate form including hydrates of Asenapine.

Pharmaceutically acceptable salts of Asenapine include salts with hydrochloric acid, sulfuric acid, phosphoric acid, hydrobromic acid, hydroiodic acid, sulfamic acid, citric acid, lactic acid, maleic acid, malic acid, succinic acid, tartaric acid, cinnamic acid, acetic acid benzoic acid, gluconic acid, ascorbic acid etc. A preferred salt is Asenapine maleate.

The term "sublingual" delivery as used herein refers to the pharmacological route of administration by which substances diffuse into the blood through tissues under the tongue.

The term "buccal" delivery as used herein refers to a topical route of administration by which drugs held or applied in the buccal area (in the cheek) diffuse through the oral mucosa and enter directly into the bloodstream.

In one embodiment, the present invention relates to a method which comprises administering via oral mucosal exposure a therapeutically effective amount of Asenapine or a pharmaceutically acceptable salt thereof to a patient in need thereof.

The term "therapeutically effective amount" as used herein means that the amount of the Asenapine contained in the composition administered is of sufficient quantity to achieve the intended purpose, such as, in this case treatment of symptoms of schizophrenia and psychosis in mammals.

An Asenapine maleate or Asenapine base or Asenapine acid salt can be delivered sublingually from a solution composition. Both crystal forms of Asenapine maleate have good solubility in an ethanol water mixture and therefore can be readily prepared in a liquid formulation for drug delivery. The solution can be made by dissolving any form of Asenapine (free base, maleate or other acid salt) in one or more solvents and optionally may contain additional pharmaceutically acceptable excipients, preservatives and diluents.

The term "pharmaceutically acceptable" as used herein means that which is useful in preparing a pharmaceutical composition that is generally safe and non-toxic.

All % of solvents herein refer to volume %, unless otherwise specified. The term "% v/v" (also written as "v/v %") means the volume of a solute in the total volume of solution. As one skilled in the art would understand, when the solute is a liquid, sometimes it is convenient to express its concentration in volume/volume percent. The calculation of "% v/v" is:

$$\text{Concentration solute (v/v \%)} = \frac{\text{volume solute (mL)}}{\text{Total volume of solution (mL)}} \times 100$$

As used herein, the term "about" is defined as ±10%, preferably ±5%.

One embodiment of the present invention relates to pharmaceutical liquid composition for buccal or sublingual administration comprising Asenapine, or a pharmaceutically acceptable salt or hydrate thereof, an alcoholic solvent, and, optionally, one or more pharmaceutically acceptable excipients.

The liquid pharmaceutical composition according to the present invention is in the form of solution, suspension, nano-suspension, emulsion, micro-emulsion, multiple emulsion and the like meant for administration through oral mucosa preferably, in the form of solution.

Another embodiment of the present invention relates to pharmaceutical liquid spray composition for buccal or sublingual administration consisting essentially of Asenapine, or a pharmaceutically acceptable salt or hydrate thereof, and an alcoholic solvent.

In another preferred embodiment, the present invention relates to pharmaceutical liquid spray compositions for buccal or sublingual administration consisting of Asenapine, or a pharmaceutically acceptable salt or hydrate thereof, an alcoholic solvent and water.

Some of the preferred solvents for use in liquid formulations of the present invention are alcohols such as ethanol or isopropanol, low molecular weight fatty acids, propylene glycol, polyethylene glycol, glycerin, water and mixtures thereof. There may more than two solvents used for a formulation preparation. Preferably, the compositions of the present invention include ethanol.

In certain embodiments, compositions containing propylene glycol were found to be unsuitable and resulted in discoloration upon storage. Accordingly, preferable compositions are free of polyols, in particular, propylene glycol.

Non-aqueous solvent may be present in an amount of about 10% to about 90%. Preferably, non-aqueous solvent is included in the composition at 10% to 80%, more preferably 20% to 80%. In certain especially preferred embodiments, the composition includes about 60% non-aqueous solvent.

An alcoholic solvent, such as ethanol, may be present in an amount of about 10% to about 90%. Preferably, from 10% to 80%, more preferably about 60%.

Optionally, the formulation may also contain menthol, flavors, sugar, artificial sweetener and soluble polyhydroxy alcohols such as mannitol and sorbitol. One can also use other suitable solvents and surfactants that are miscible with water.

The present invention further comprises other pharmaceutically acceptable excipients selected from one or more of preservatives, buffers, taste modifiers, flavors or combinations thereof.

Preservatives as used in the present compositions may be selected from one or more of benzalkonium chloride, benzyl alcohol, chlorobutanol, cresol, ethyl alcohol, thiomersal, parabens, benzoic acid, EDTA, sodium benzoate and the like thereof.

Preservatives may be included in the compositions from about 0.01% to about 0.1%, preferably about 0.01% to about 0.02%.

Antioxidants as used in the present compositions may be selected from one or more of e.g. sulfites, amino acids, such as L-methionine, ascorbic acid and a-tocopherol. Preferably, the antioxidant is L-methionine.

Antioxidants may be included in the compositions from about 0.01% to about 0.1%, preferably about 0.01% to about 0.02%.

Buffers as used in the present invention include an acid or a base and its conjugate base or acid, respectively. Suitable buffers include mixtures of weak acids and alkali metal salts (e.g., sodium, potassium) of the weak acids, such as acetate, citrate, tartarate, phosphate, benzoate and bicarbonate buffers and combinations thereof.

pH regulating agents including buffers such as acetate, citrate, phosphate, borate, carbonate etc, sodium hydroxide, hydrochloric acid etc. Anti-nucleating agents may be included as well.

Taste modifiers used in the present invention increases the patient acceptability and are selected from one or more of ion exchange resins, polyvinyl pyrrolidone and/or copolyvidone, a high molecular weight polyethylene glycol, sweetening agents such as monosaccharides, disaccharides, sugar alcohols, and polysaccharides, e.g., glucose, fructose, invert sugar, sorbitol, sucrose, maltose, xylose, ribose, mannose, corn syrup solids, xylitol, mannitol, maltodextrins, and mixtures thereof, artificial sweeteners and dipeptide-based sweeteners such as saccharin salts, acesulfame K, sucralose, aspartame, and mixtures thereof.

Flavors may optionally be used in the present invention selected from one or more naturally derived oils from plants, flowers, leaves, nature identical, artificial flavoring compounds such as synthetic flavor oils.

It is important to deliver the efficacious amount of the drug in a relatively small amount of dosing medium. Thus the solubility of the Asenapine or its salt in the final dosing solution is an important consideration.

The composition of the present invention can contain about 0.5-20 mg of Asenapine in a total volume of 50-500 μL per dose. More preferably, about 3-15 mg of Asenapine in a total volume of 50-250 μL per dose. Most preferably, the compositions include 2.5-10 mg of Asenapine in a total volume of 100 to 250 μL per dose. In certain preferred embodiments, the composition delivers about 5 mg or about 10 mg Asenapine in about 140 μL per dose.

It will be understood that these amounts may be adjusted for the precise delivery of therapeutic dose. Since the drug is delivered in a solution, disintegration and dissolution in the saliva is not required and the drug can be quickly absorbed in the mouth. The solution formulation of the present invention allows one to have a very precise control of the amount administered.

The Asenapine dosing solution of the present invention can be made with either H or L crystal form of the drug or a mixture of any crystalline or amorphous non-crystalline forms of the drug substance. In addition, it does not require any special manufacturing equipment or procedures. To make the dosing solution of the present invention, one simply dissolves any form of Asenapine in desired solvent composition with the pH adjusted in the range of 5 to 9. In one embodiment, the Asenapine active ingredient is in the form of Asenapine maleate. Additional adjuvants can be added to the formulation for desired taste and mouth feel. The solution may be further processed as desired to prepare the final dosing composition. The solution is filtered and filled in the container directly and delivery pump inserted on the container to produce a delivery device.

The formulations are stable for an extended period of time at normal storage conditions. As used herein, "stable" is defined as no more than about a 10% loss of Asenapine under typical commercial storage conditions. Preferably, formulations of the present inventions will have no more than about a 10% loss of Asenapine, more preferably, no more than about a 5% loss of Asenapine, under typical commercial storage conditions.

As used herein, an "extended period of time" means 3 months or greater.

Storage conditions refers to those long term, intermediate and accelerated conditions discussed in ICH guidelines for stability testing of active pharmaceutical ingredients and finished pharmaceutical products (WHO 2009), the contents of which are incorporated herein by reference. Namely, storage conditions include 5° C.±3° C., 25° C.±2° C./60% RH±5% RH, 30° C.±2° C./65% RH±5% RH, and 40° C.±2° C./75% RH±5% RH. As used herein, storage of compositions refers to storage within a container closure system. Storage conditions can also refer to ambient conditions.

The term "ambient" as used herein refers to uncontrolled atmospheric conditions in the room or place. For purposes of experiments conducted by the inventors, ambient laboratory conditions aimed to achieve 25° C.±2° C./60% RH±5% RH. However, such conditions were not strictly maintained and monitored in the ambient environment.

Analysis of the liquid formulations of the present invention can be performed using techniques known in the art, including, for example, HPLC, gas chromatography, and NMR. After exposure to typical commercial storage conditions, analysis of the formulations of the present invention will indicate that the formulation contains no less than about 90% of the amount of Asenapine present prior to exposure to the storage conditions. Preferably, analysis will indicate that the formulation contains no less than about 95% of the amount of Asenapine present prior to exposure to the storage conditions. More preferably, analysis will indicate that the formulation contains no less than about 98% of the amount of Asenapine prior to exposure to the storage conditions.

In preferred embodiments of the present invention, analysis of the formulations of the present invention will indicate that the formulation contains no less than about 90% of the amount of Asenapine present prior to exposure to storage conditions that include temperatures of about 25° C. and time periods of about 30 days (about 1 month) to about 365 days (about 1 year). Preferably, analysis of the formulations of the present invention will indicate that the formulation contains no less than about 90% of the amount of Asenapine present prior to exposure to storage conditions that include temperatures of about 25° C. and time periods of about 30 days (about 1 month), about 90 days (about 3 months), and about 180 days (about 6 months). Preferably, analysis will indicate that the formulation contains no less than about 95% of the amount of Asenapine present prior to exposure to storage conditions that include temperatures of about 25° C. and time periods of about 30 days (about 1 month) to about 365 days (about 1 year). More preferably, analysis will indicate that the formulation contains no less than about 95% of the amount of Asenapine present prior to exposure to storage conditions that include temperatures of about 25° C. and time periods of about 30 days (about 1 month), about 90 days (about 3 months), about 180 days (about 6 months).

In preferred embodiments of the present invention, analysis of the formulations of the present invention will indicate that the formulation contains no less than about 90% of the amount of Asenapine present prior to exposure to storage conditions that include temperatures of about 40° C. and time periods of about 30 days (about 1 month) to about 365 days (about 1 year). Preferably, analysis of the formulations of the present invention will indicate that the formulation contains no less than about 90% of the amount of Asenapine present prior to exposure to storage conditions that include temperatures of about 40° C. and time periods of about 30 days (about 1 month), about 90 days (about 3 months), and about 180 days (about 6 months). Preferably, analysis will indicate that the formulation contains no less than about 95% of the amount of Asenapine present prior to exposure to storage conditions that include temperatures of about 40° C. and time periods of about 30 days (about 1 month) to about 365 days (about 1 year). More preferably, analysis will indicate that the formulation contains no less than about 95% of the amount of Asenapine present prior to exposure to storage conditions that include temperatures of about 40° C. and time periods of about 30 days (about 1 month), about 90 days (about 3 months), about 180 days (about 6 months), about 240 days (about 9 months), and about 365 days (about 1 year).

The therapeutic solution of this invention may be dosed under the tongue as a spray or a mist using an appropriate delivery device that is known in the art.

The formulations of present invention may be administered orally once, twice or three times daily to a subject for the treatment of psychiatric disorders.

A further embodiment of the present invention relates to process for the preparation of pharmaceutical composition comprising Asenapine comprising the steps of dissolving Asenapine, or a pharmaceutically acceptable salt or hydrate thereof, in an ethanolic solution, optionally, adding a solution of EDTA and/or a solution of L-Methionine to the ethanolic Asenapine solution, stirring the mixture under $N_2$, filtering the resulting mixture, and filing the filtrate into a storage container.

In some embodiments, the present invention provides a novel method for the treatment of schizophrenia and psychosis by spraying a composition of Asenapine for sublingual or buccal use. Spraying devices are capable of producing dosing droplets of varying sizes and one can arrive at an appropriate droplet size and volume by changing the delivery pump system. The sublingual spray unit may deliver a single dose or may be used to deliver up to 100 doses of the drug from one unit. Each specific application of the drug may require a different type of spray pump unit. Thus a spray unit for an adult use may be different than the one for pediatric application. Each specific dose of the drug may have its own special sublingual delivery device.

Sprays and aerosols

In spray and aerosol compositions, Asenapine is delivered to the mouth in a dosed amount through a nozzle or orifice. The composition may be delivered through a pump spray, a pressurized spray or as an aerosol.

Moreover, it is easy to apply and it is possible to ensure the delivery of the composition to the oral mucosa.

A spray or aerosol composition may contain a suitable amount of one or more propellants in an organic solvent. In order to apply a spray or an aerosol to the mouth, the composition normally contains one or more volatile solvents that evaporate upon application to the skin.

A wide variety of spray devices are known in the art. Such pumps can be propelled with or without air.

Propellants that provide a suitable pressure within an aerosol dispenser include hydrocarbons such as propane, butane, isobutene, or dimethylether; hydrofluorocarbons (e.g. hydrofluoroalkanes) and hydrochloroflurocarbons (e.g. hydrochlorofluroalkanes) such as dichlorodifluoromethane, trichloromonofluromethane, dichlorofluroethan, monochlorodifluromethane, dichlorotetrafluoroethane, difluroethane, tetrafluorethane, heptafluropropane or combinations thereof; or compressed gases such as nitrogen or carbon dioxide or combinations thereof. Such propellants may also be used in spray systems.

In another embodiment, the present invention relates to liquid compositions of Asenapine for administration via metered dispensing system for increased bioavailability wherein, the said metered dispensing system is a spray pump and/or an actuator system with simple, user-friendly operation to deliver precise dose over buccal mucosa. Suitable devices are commercially available from Aptar Pharma. A particularly preferred multidose device is the APTAR, #31066705 with ACT31054040.

The present invention is expected to increase retention of the formulation in contact with the oral mucosa resulting in higher bioavailability and also has enhanced ease of usage provided by a spray pump and/or an actuator system with simple, user-friendly operation to deliver precise dose of Asenapine.

EXAMPLES

HPLC Procedure for Analysis of Asenapine Formulations

Column: Inertsil C8-3, 4.6×250 mm, 5 μm or equivalent column (USP packing L7, Waters).

Solvent A: Weigh accurately 3.48 g of anhydrous Potassium Phosphate Dibasic ($K_2HPO_4$) and transfer into a suitable container. Add 1000 ml of Milli-Q water and then add 0.5 mL of Triethylamine. Mix for 15 to 30 minutes and adjust pH 6.7±0.05 with Orthophosphoric acid ($H_3PO_4$). Filter through 0.45 μm filter and degas.

Solvent B: Mix 90% Acetonitrile (MeCN), 10% Water filter and degas.

Mobile Phase: Isocratic; 38% Solvent A, 62% Solvent B
Wavelength: 220 nm
Flow Rate: 1.0 ml/min
Column Temperature: 40° C.
Injection Volume: 20 μL
Run Time: 40 min Sample Preparation: Dilute the test solution with diluent (50% Acetonitirile, 50% Water) to prepare a sample with concentration of about 1.5 mg/mL of Asenapine. Dilution of 2 ml solution of 10 mg/0.140 ml Asenapine to 100 ml gives a sample of about 1.43 mg/ml.

Results:

Percent of each Asenapine related compound is calculated against average peak area of Asenapine low level working standard (concentration about 7.5 μg/ml Asenapine) using the equation below:

$$\% \text{ impurity} = \frac{Ru}{Rs} \times \frac{\text{Standard Concentration}}{\text{Sample Concentration}} \times \frac{1}{RRF} \times 100\% \times 1000$$

Where,
Ru=Area of impurity peak
Rs=Average working standard peak area of Asenapine Standard Concentration is in μg/ml and Sample Concentration is in mg/ml
RRF=Relative response factor (use RRF=1 for all unspecified impurities)

Ignore any peak in the void volume (~2.5 min) and the peak due to Maleic acid at RT=~2.45 min. Molecular weight of Asenapine Maleate=401.84 Molecular weight of Asenapine=285.77.

HPLC Retention Times and Structures of Asenapine and Impurities

| No | Name | RT (min) | RRT | RRF | Structure |
|---|---|---|---|---|---|
| 1 | Asenapine N-Oxide | 4.2 | 0.28 | 1.10 | 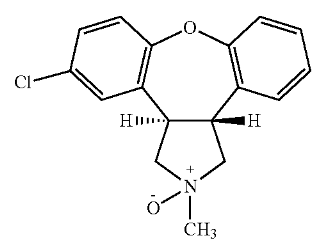 |
| 2 | Deschloro Asenapine | 9.1 | 0.61 | 0.87 | 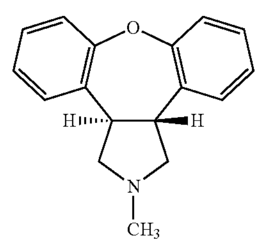 [SMILES: CN1C[C@H]2c3ccccc3Oc3ccccc3[C@@H]2C1] |
| 3 | Asenapine | 15 | 1 | 1.00 | 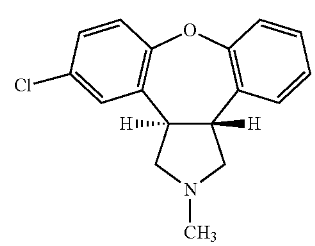 [SMILES: CN1C[C@H]2c3ccccc3Oc3ccc(Cl)cc3[C@@H]2C1] |

Example 1

Preparation of Asenapine, 10 mg/0.140 ml Solution in 50% Alcohol-water

Ethyl Alcohol (100%) and water were mixed in a 50:50 (v/v) ratio and the solution was degassed by purging with $N_2$ for 60 min before using for compounding. To 80 ml of this solution, 10.043 g of Asenapine Maleate was added and stirred for 5-10 min at ~400 RPM until a clear solution was formed. Separately, stock solutions of EDTA (100 mg/ 3 ml) and L-Methionine (100 mg/3 ml) were prepared. To the solution of Asenapine maleate prepared above, 0.3 ml of EDTA and 0.3 ml of L-Methionine stock solutions were added and stirred for 2 min. The volume of the Asenapine solution was adjusted to 100 ml by adding additional alcohol/water. After stirring under $N_2$ for 5 min the solution was filtered using 0.2 µM PVDF filter and the filtrate was filled in containers, flushed with $N_2$ and sealed. The containers were kept on stability and analyzed at various time points.

Example 2

Preparation of Asenapine, 10 mg/0.140 ml Solution in 60% Alcohol-water

Ethyl Alcohol (100%) and water were mixed in a 60:40 (v/v) ratio and the solution was degassed by purging with $N_2$ for 60 min. This solution was used for compounding. To 80 ml of this solution, 10.043 g of Asenapine Maleate was added and stirred for 5-10 min at ~400 RPM until a clear solution is formed. Separately, stock solutions of EDTA (100 mg/ 3 ml) and L-Methionine (100 mg/3 ml) were prepared. To the solution of Asenapine maleate prepared above, 0.3 ml of EDTA and 0.3 ml of L-Methionine stock solutions were added and stirred for 2 min. The volume of the Asenapine solution was adjusted to 100 ml by adding additional alcohol/water. After stirring under $N_2$ for 5 min the solution was filtered using 0.2 µM PVDF filter and the filtrate was filled in containers, flushed with $N_2$ and sealed. The containers were kept on stability and analyzed at various time points.

Example 3

Preparation of Asenapine, 5 mg/0.140 ml Solution in 50% Alcohol-water

Ethyl Alcohol (100%) and water were mixed in a 50:50 (v/v) ratio and the solution was degassed by purging with $N_2$ for 60 min. This solution was used for compounding. To 80 ml of this solution, 5.021 g of Asenapine Maleate was added and stirred for 5-10 min at ~400 RPM until a clear solution is formed. Separately, stock solutions of EDTA (100 mg/ 3 ml) and L-Methionine (100 mg/ 3 ml) were prepared. To the solution of Asenapine maleate prepared above, 0.3 ml of EDTA and 0.3 ml of L-Methionine solutions were added and stirred for 2 min. The volume of the Asenapine solution was made up to 100 ml by adding additional alcohol/water. After stirring under $N_2$ for 5 min the solution was filtered using 0.2 µM PVDF filter and the filtrate was filled in containers, flushed with $N_2$ and sealed. The containers were kept on stability and analyzed at various time points.

Other solutions of Asenapine maleate in alcohol/water with different ratios of 100% ethyl alcohol and water with varying amounts of Asenapine were prepared by analogous methods.

The stability of these formulations at 25° C. and 40° C. was studied and is listed in the table below.

Stability of Asenapine Spray Formulations

| Formulation | Potency (mg/0.14 ml) | Stability Condition | Assay | Related Compounds (%) | | Total Impurity |
|---|---|---|---|---|---|---|
| | | | | 0.28 RRT | 0.61 RRT | |
| Ethanol:Water 80:20 | 10 | Initial | | 0.06 | 0.05 | 0.11 |
| | | 3M@ 25° C. | 99.4 | NQ | 0.05 | 0.05 |
| | | 6M@ 25° C. | 101.1 | 0.06 | 0.05 | 0.17 |
| | | 3M@ 40° C. | 101.9 | 0.12 | 0.04 | 0.16 |
| | | 6M@ 40° C. | 99.4 | 0.29 | 0.04 | 0.88 |
| Ethanol:Water 50:50 | 10 | Initial | | | | |
| | | 3M@ 25° C. | 105.2 | | | |
| | | 6M@ 25° C. | 103.7 | 0.04 | 0.05 | 0.09 |
| | | 6M@ 40° C. | 103.7 | 0.2 | 0.05 | 0.33 |
| Ethanol:Water 60:40 | 10 | Initial | | | 0.05 | 0.05 |
| | | 3M@ 25° C. | 102.3 | 0.03 | 0.05 | 0.08 |
| | | 3M@ 40° C. | 102 | 0.1 | 0.05 | 0.24 |
| Ethanol:Water 70:30 | 10 | Initial | | | 0.05 | 0.05 |
| | | 3M@ 25° C. | 101.1 | 0.03 | 0.05 | 0.08 |
| | | 3M@ 40° C. | 102.3 | 0.09 | 0.05 | 0.22 |
| Ethanol:Water:propylene glycol 80:10:10 | 10 | Initial | | 0.07 | 0.05 | 0.18 |
| | | 3M@ 25° C. | | 0.05 | 0.05 | 0.18 |
| | | 6M@ 25° C. | 101.8 | 0.07 | 0.05 | 0.22 |
| | | 3M@ 40° C. | | 0.11 | 0.05 | 0.55 |
| | | 6M@ 40° C. | 100.3 | 0.16 | 0.04 | 0.99 |

Formulations with glycol were not suitable due to light yellow color formation upon storage.

Example 4

Study of solvent Loss from Asenapine Solution Stored in Spray Pump

A solution of Asenapine (10 mg/0.14 ml) in 60:40 alcohol/water was prepared as in example 2 and 10 ml of this solution was filled in a 15 ml bottle then attached to a 0.140 ml output spray pump (APTAR, #31066705+ ACT31054040). The initial weights of filled unit and solution alone were recorded. The weight loss was studied at 25° C./60% RH for 35 days. The percentage weight loss on different days was calculated as follow;

$$\% \text{ weight loss} = \frac{\text{weight of filled bottle at Day 0} - \text{weight of filled bottle on specific Day}}{\text{Initial weight of solution}} \times 100$$

Similarly, a solution of Asenapine (10 mg/0.14 ml) in 90:10 alcohol/water was filled in another spray unit and loss of solvent from this unit at 25° C./60% RH was also studied.

Solvent Loss for Asenapine Solutions in Alcohol: Water 60:40 and 90:10 at 25° C./60% RH

| Day | % Weight Loss 60% ethanol | % Weight Loss 90% ethanol |
|---|---|---|
| 0 | | |
| 7 | 0.00 | 0.011 |
| 14 | 0.011 | 0.056 |
| 21 | 0.033 | 0.123 |
| 28 | 0.055 | 0.167 |
| 35 | 0.065 | 0.212 |

There is negligible evaporation of solvent from Asenapine solutions in ethanol-water stored in multidose spray pumps over 35 days. The loss of solvent over 35 days from 60:40 ethanol-water solution was less than solvent loss from 90:10 ethanol-water solution of Asenapine.

Example 5

Study of Dose Uniformity of Asenapine Solution from Multidose Spray Unit

A solution of Asenapine (10 mg/0.14 ml) in 60:40 alcohol: water was prepared as in example 2. A 15 ml dosing bottle was filled with 11.2 ml of this solution and attached to a 0.14 ml output pump (APTAR, #31066705+ACT31054040). The pump was primed (4-7 times) until a uniform fine mist output was achieved and weighed. The pump was kept at room temperature. The pump was actuated and weighed after each discharge. The dispensed volume for each dose was calculated by dividing the weight loss for the dose by density of solution. The results are an average from measurements from five individual multi dose spray units at each point.

Average Dispensed Volume of Asenapine Solution

| Dose No | Average Dispensed Volume (µl) (n = 5) |
|---|---|
| 1 | 141.0 |
| 10 | 139.8 |
| 20 | 143.7 |
| 30 | 142.3 |
| 40 | 141.3 |
| 50 | 139.6 |

It is envisioned that the pharmaceutical formulations and preparations of the present invention can be administered in combination with other agents where the other agents are given prior to, concurrently with, or subsequent to the administration of the formulations or preparations of the present invention. Pharmaceutically acceptable agents are known in the art.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A pharmaceutically acceptable liquid composition of Asenapine for sublingual or buccal delivery comprising:
   Asenapine, or a pharmaceutically acceptable salt or hydrate thereof;
   ethanol; and
   water,
   wherein the composition is free of a polyol and is stable for an extended period of time at normal storage conditions.

2. The composition of claim 1, wherein the composition comprises greater than about 10% by volume of ethanol.

3. The composition of claim 2, wherein the composition comprises about 10% to about 80% by volume of ethanol.

4. The composition of claim 3, wherein the composition comprises about 50% to about 70% by volume of ethanol.

5. The composition of claim 1, wherein the Asenapine, or a pharmaceutically acceptable salt or hydrate thereof, is Asenapine maleate.

6. The composition of claim 1, further comprising pharmaceutically acceptable excipients selected from one or more of preservatives, buffers, taste modifiers, flavors or combinations thereof.

7. The composition of claim 6, wherein the composition comprises EDTA.

8. The composition of claim 6, wherein the composition comprises L-Methionine.

9. The composition of claim 1, wherein the composition exhibits less than 0.3% weight loss after storage at 25° C./60% RH for up to 35 days.

10. The composition of claim 9, wherein the composition exhibits less than 0.07% weight loss after storage at 25° C./60% RH for up to 35 days.

11. A pharmaceutically acceptable liquid composition of Asenapine for sublingual or buccal delivery comprising:
   Asenapine, or a pharmaceutically acceptable salt or hydrate thereof;
   greater than about 10% ethanol; and
   water; wherein the composition is free of a polyol.

12. The composition of claim 11, wherein the Asenapine, or a pharmaceutically acceptable salt or hydrate thereof, is Asenapine maleate.

13. The composition of claim 11, wherein the composition comprises about 10% to about 80% by volume of ethanol.

14. The composition of claim 13, wherein the composition comprises about 50% to about 70% by volume of ethanol.

15. The composition of claim 11, further comprising pharmaceutically acceptable excipients selected from one or more of preservatives, buffers, taste modifiers, flavors or combinations thereof.

16. A method of treating psychosis by administering a therapeutically effective amount of a composition of claim 1 to a patient in need thereof.

17. The method of claim 16, wherein about 2.5 mg to about 10 mg Asenapine is delivered to the patient's mouth.

18. The method of claim 17, wherein an average dispensed volume of about 140 µL of the composition is administered to the patient by spraying the composition into the patient's mouth.

19. A kit for treating psychosis by administering a pharmaceutically acceptable liquid composition of Asenapine to oral mucosa comprising:
    a formulation including Asenapine, or a pharmaceutically acceptable salt or hydrate thereof, ethanol, and water; and
    a multidose pump filled with the formulation; wherein the composition is free of a polyol.

* * * * *